United States Patent [19]

Sauerberg et al.

[11] Patent Number: 5,919,805
[45] Date of Patent: *Jul. 6, 1999

[54] HETROCYCLIC COMPOUNDS AND THEIR PREPARATION AND USE

[75] Inventors: Per Sauerberg, Valby; Preben H. Olesen, Copenhagen; Charles H. Mitch, Columbus, all of Denmark

[73] Assignee: Novo Nordisk A/S, Novo Alle, Denmark

[ * ] Notice: This patent is subject to a terminal disclaimer.

[21] Appl. No.: 08/874,054

[22] Filed: Jun. 12, 1997

Related U.S. Application Data

[62] Division of application No. 08/453,605, May 30, 1995, Pat. No. 5,658,932, which is a division of application No. 08/362,031, Dec. 22, 1994, Pat. No. 5,571,826, which is a division of application No. 08/026,708, Mar. 5, 1993, Pat. No. 5,376,668, which is a continuation-in-part of application No. 07/745,033, Aug. 14, 1991, Pat. No. 5,328,924.

[30] Foreign Application Priority Data

Aug. 21, 1990 [DK] Denmark .................................. 1983/90

[51] Int. Cl.$^6$ .......................... A61K 31/44; C07D 417/04
[52] U.S. Cl. .......................... 514/340; 514/342; 546/256; 546/270; 546/277
[58] Field of Search ..................................... 514/340, 333, 514/342; 546/256, 270, 277

[56] References Cited

U.S. PATENT DOCUMENTS

| 5,041,455 | 8/1991 | Sauerberg et al. ...................... 514/342 |
| 5,043,345 | 8/1991 | Sauerberg et al. ...................... 514/342 |

FOREIGN PATENT DOCUMENTS

| 0 316 718 | 5/1985 | European Pat. Off. . |
| 0 239 309 | 9/1987 | European Pat. Off. . |
| 0 244 018 | 11/1987 | European Pat. Off. . |
| 0 296 721 | 12/1988 | European Pat. Off. . |
| 0 301 729 | 2/1989 | European Pat. Off. . |
| 0 307 142 | 3/1989 | European Pat. Off. . |
| 0 322 182 | 6/1989 | European Pat. Off. . |
| 0 328 200 | 8/1989 | European Pat. Off. . |
| 0 349 956 | 1/1990 | European Pat. Off. . |
| 0 384 285 | 8/1990 | European Pat. Off. . |

*Primary Examiner*—Zohreh Fay
*Attorney, Agent, or Firm*—Steve T. Zelson; Elias J. Lambiris; Carol E. Rozek

[57] ABSTRACT

The present invention relates to therapeutically active azacyclic compounds, a method of preparing the same and to pharmaceutical compositions comprising the compounds. The novel compounds are useful as stimulants of the cognitive function of the forebrain and hippocampus of mammals and especially in the treatment of Alzheimer's disease, severe painful conditions and glaucoma.

25 Claims, No Drawings

HETEROCYCLIC COMPOUNDS AND THEIR PREPARATION AND USE

CROSS-REFERENCE TO RELATED APPLICATION

This application is a divisional of application Ser. No. 08/453,605 filed May 30, 1995 now U.S. Pat. No. 5,658,932, which is a divisional of application Ser. No. 08/362,031 filed Dec. 22, 1994 now U.S. Pat. No. 5,571,826, which is a divisional of application Ser. No. 08/026,708 filed Mar. 5, 1993 now U.S. Pat. No. 5,376,668, which is a continuation-in-part of Ser. No. 07/745,033 filed Aug. 14, 1991 now U.S. Pat. No. 5,326,924.

BACKGROUND OF THE INVENTION

1. Field of the Invention

The present invention relates to therapeutically active azacyclic compounds, a method of preparing the same and to pharmaceutical compositions comprising the compounds.

The novel compounds are useful as stimulants of the cognitive function of the forebrain and hippocampus of mammals and especially in the treatment of Alzheimer's disease.

2. Description of Related Art

Due to the in general improved health situation in the western world, elderly-related diseases are much more common now than in the past and are likely to be even more common in the future.

One of the elderly-related symptoms is a reduction of the cognitive functions. This symptom is especially pronounced in the pathophysiological disease known as Alzheimer's disease. This disease is combined with, and also most likely caused by, a up to 90% degeneration of the muscarinic cholinergic neurons in nucleus basalis, which is part of substantia innominata. These neurons project to the prefrontal cortex and hippocampus and have a general stimulatory effect on the cognitive functions of the forebrain as well as of hippocampus, namely learning, association, consolidation and recognition.

It is a characteristic of Alzheimer's disease that although the cholinergic neurons degenerate, the postsynaptic muscarinic receptors in the forebrain and hippocampus still exist. Therefore muscarinic cholinergic agonists are useful in the treatment of Alzheimer's disease and in improving the cognitive functions of elderly people.

It is well known that arecoline (methyl 1-methyl-1,2,5,6-tetrahydropyridine-3-carboxylate) is such a cholinergic agonist.

Arecoline however has a very short biological half life and a small separation between central and peripheral muscarinic effects. Furthermore arecoline is a rather toxic compound.

EP-A-0307142 discloses a class of thiadiazoles, substituted on one of the ring carbon atoms with a non-aromatic azacyclic or azabicyclic ring system, and substituted on the other ring carbon atom with a substituent of low lipophilicity, or a hydrocarbon substituent, which are muscarinic agonists and therefore useful in the treatment of neurological and mental illnesses and severe painful conditions.

It is an object of the invention to provide new muscarinic cholinergic compounds.

SUMMARY OF THE INVENTION

The novel compounds of the invention are heterocyclic compounds having the formula I

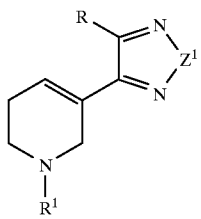

(I)

wherein $Z^1$ is oxygen or sulphur;

R is $—Z^2R^2$, $—SOR^2$, $—SO_2R^2$, $—Z^2—R^2—Z^3—R^3$, $—Z^2—R^2—CO—R^3$, $—Z^2—R^2—CO_2—R^3$, $—Z^2—R^2—O_2C—R^3$, $—Z^2—R^2—CONH—R^3$, $—Z^2—R^2—NHCO—R^3$, $—Z^2—R^2—X$, $Z^2—R^2—Z^3—X$ wherein $Z^2$ and $Z^3$ independently are oxygen or sulphur, and $R^2$ and $R^3$ independently are straight or branched $C_{1-15}$-alkyl, straight or branched $C_{2-15}$-alkenyl, straight or branched $C_{2-15}$-alkynyl, each of which is optionally substituted with halogen, —OH, —CN, —CF_3, one or two phenyl, phenoxy, benzoyl, or benzyloxycarbonyl groups wherein each aromatic group is optionally substituted with halogen, —CN, $C_{1-4}$-alkyl or $C_{1-4}$-alkoxy, wherein X is a 5 or 6 membered heterocyclic group containing one to four N, O or S atoms) or a combination thereof, which heterocyclic group is optionally which heterocyclic group is optionally substituted at a carbon or nitrogen atom with straight or branched $C_{1-6}$-alkyl, phenyl, benzyl or pyridine, or a carbon atom in the heterocyclic group together with an oxygen atom form a carbonyl group, or which heterocyclic group is optionally fused with a phenyl group; and $R^1$ is hydrogen, straight or branched $C_{1-5}$-alkyl, straight or branched $C_{2-5}$-alkenyl or straight or branched $C_{2-5}$-alkynyl; or a pharmaceutically acceptable salt thereof.

Examples of such salts include inorganic and organic acid addition salts such as hydrochloride, hydrobromide, sulphate, phosphate, acetate, fumarate, maleate, citrate, lactate, tartrate, oxalate, or similar pharmaceutically acceptable inorganic or organic acid addition salt.

The compounds of this invention are also useful analgesic agents and therefore useful in the treatment of severe painful conditions.

Furthermore, the compounds of this invention are useful in the treatment of glaucoma.

The invention also relates to methods of preparing the above mentioned compounds, comprising:

a) alkylating a compound of formula II

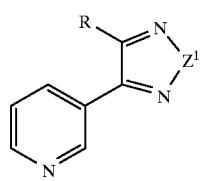

(II)

wherein $Z^2$ and R have the meaning defined above with an alkyl halide and reducing the compound thus formed with hydride ions to form a compound of formula I

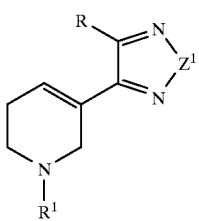

(I)

wherein $Z^1$, $Z^2$, R and $R^1$ have the meanings defined above, or b) oxidizing a compound of formula III

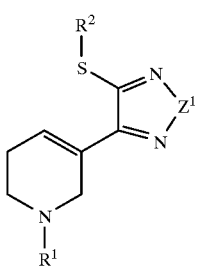

(III)

wherein $Z^2$, $R^1$ and $R^2$ have the meanings defined above by standard procedures to form a compound of formula IV

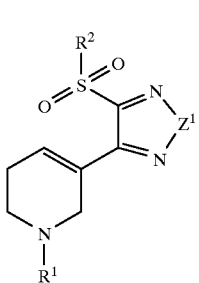

(IV)

and subsequent displacement of $-SO_2-R^2$ with an appropriate nucleophile to form a compound of formula I.

It is to be understood that the invention extends to each of the stereoisomeric forms of the compounds of formula I as well as the racemates.

The pharmacological properties of the compounds of the invention can be illustrated by determining their capability to inhibit the specific binding of $^3$H-Oxotremorine-M ($^3$H-Oxo). Birdsdall N. J. M., Hulme E. C., and Burgen A. S. V. (1980). "The Character of Muscarinic Receptors in Different Regions of the Rat Brain". Proc. Roy. Soc. London (Series B) 207,1.

$^3$H-Oxo labels muscarinic receptor in the CNS (with a preference for agonist domains of the receptors). Three different sites are labelled by $^3$H-Oxo. These sites have affinity of 1.8, 20 and 3000 nM, respectively. Using the present experimental conditions only the high and medium affinity sites are determined.

The inhibitory effects of compounds on $^3$H-oxo binding reflects the affinity for muscarinic acetylcholine receptors.

All preparations are performed at 0–4° C. unless otherwise indicated. Fresh cortex (0.1–1 g) from male Wistar rats (150–250 g) is homogenized for 5–10 s in 10 ml 20 mM Hepes pH: 7.4, with an Ultra-Turrax homogenizer. The homogenizer is rinsed with 10 ml of buffer and the combined suspension centrifuged for 15 min at 40,000×g. The pellet is washed three times with buffer. In each step the pellet is homogenized as before in 2×10 ml of buffer and centrifuged for 10 min at 40,000×g.

The final pellet is homogenized in 20 mM Hepes pH: 7.4 (100 ml per g of original tissue) and used for binding assay. Aliquots of 0.5 ml is added 25 μl of test solution and 25 μl of $^3$H-Oxotremorine (1.0 nM, final concentration) mixed and incubated for 30 min at 25° C. Non-specific binding is determined in triplicate using arecoline (1 μg/ml, final concentration) as the test substance. After incubation samples are added 5 ml of ice-cold buffer and poured directly onto Whatman GF/C glass fibre filters under suction and immediately washed 2 times with 5 ml of ice-cold buffer. The amount of radioactivity on the filters are determined by conventional liquid scintillation counting. Specific binding is total binding minus non specific binding.

Test substances are dissolved in 10 ml water (if necessary heated on a steam bath for less than 5 minutes) at a concentration of 2.2 mg/ml. 25–75% inhibition of specific binding must be obtained before calculation of $IC_{50}$.

The test value will be given as $IC_{50}$ (the concentration (ng/ml) of the test substance which inhibits the specific binding of $^3$H-Oxo by 50%).

$IC_{50}$=(applied test substance concentration)

$$IC_{50} = (\text{applied test substance concentration}) \times \frac{1}{\left(\frac{C_o}{C_x} - 1\right)} \text{ ng/l}$$

where $C_o$ is specific binding in control assays and $C_x$ is the specific binding in the test assay. (The calculations assume normal mass-action kinetics).

Test results obtained by testing some compounds of the present invention will appear from the following table 1.

TABLE 1

| Compound No. | Inhibition in vitro OXO BINDING (ng/ml) |
|---|---|
| 1 | 0.39 |
| 2 | 0.47 |
| 3 | 1.2 |
| 4 | 0.43 |
| 5 | 0.54 |
| 6 | 0.33 |
| 7 | 1.1 |
| 8 | 0.44 |
| 10 | 1.0 |
| 11 | 3.2 |
| 12 | 7.2 |
| 13 | 14 |
| 14 | 18 |
| 15 | 8.2 |
| 16 | 5.9 |
| 17 | 4.9 |
| 18 | 6.4 |
| 20 | 1.8 |
| 21 | 3.9 |
| 22 | 2.1 |
| 23 | 2.0 |
| 24 | 7.9 |
| 26 | 10 |
| 27 | 5 |
| 28 | 1.6 |
| 29 | 3.0 |
| 30 | 5.4 |
| 31 | 4.3 |
| 32 | 0.62 |

TABLE 1-continued

| Compound No. | Inhibition in vitro OXO BINDING (ng/ml) |
|---|---|
| 33 | 13 |
| 34 | 1.6 |
| 35 | 5.2 |
| 36 | 6.4 |
| 37 | 4.5 |
| 38 | 20 |
| 39 | 9.2 |
| 40 | 2.1 |
| 41 | 12 |
| 43 | 285 |
| 44 | 19 |
| 45 | 10 |
| 47 | 26 |
| 49 | 2.1 |
| 50 | 0.37 |
| 51 | 0.47 |
| 52 | 1.9 |
| 53 | 3.8 |
| 54 | 0.54 |
| 55 | 16 |
| 56 | 1.0 |
| 57 | 1.0 |
| 58 | 0.6 |
| 59 | 3.9 |
| 61 | 100 |
| 62 | 5.4 |
| 66 | 2.1 |
| 67 | 0.30 |
| 68 | 0.47 |
| 69 | 0.43 |
| 71 | 1.3 |
| 72 | 0.92 |
| 73 | 19 |
| 74 | 2.1 |

The compounds of the invention, together with a conventional adjuvant, carrier, or diluent, and if desired in the form of a pharmaceutically acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective muscarinic cholinergic agonistic amount of the active ingredient commensurate with the intended daily dosage range to be employed. Tablets containing ten (10) milligrams of the active ingredient or, more broadly, one (1) to hundred (100) milligrams, per tablet, are accordingly suitable representative unit dosage forms.

The compounds of this invention can thus be used for the formulation of pharmaceutical preparations, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethyl cellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil. Ampoules are convenient unit dosage forms. Tablets, dragees, or capsules having talc and/or a carbohydrate carrier or binder or the like, the carrier preferably being lactose and/or corn starch and/or potato starch, are particularly suitable for oral application. A syrup, elixir of the like can be used in cases where a sweetened vehicle can be employed.

Generally, the compounds of this invention are dispensed in unit form comprising 1–100 mg in a pharmaceutically acceptable carrier per unit dosage.

The dosage of the compounds according to this invention is 1–100 mg/day, preferably 10–70 mg/day, when administered to patients, e.g. humans, as a drug.

A typical tablet which may be prepared by conventional tabletting techniques contains:

| | | |
|---|---|---|
| Active compound | 5.0 | mg |
| Lactosum | 67.8 | mg Ph.Eur. |
| Avicel ® | 31.4 | mg |
| Amberlite ® | 1.0 | mg |
| Magnesii stearas | 0.25 | mg Ph.Eur. |

Due to the high muscarinic cholinergic receptor agonistic activity, the compounds of the invention are extremely useful in the treatment symptoms related to a reduction of the cognitive functions of the brain of mammals, when administered in an amount effective for stimulating the cognitive functions of the forebrain and hippocampus. The important stimulating activity of the compounds of the invention includes both activity against the pathophysiological disease, Alzheimer's disease as well as against normal degeneration of brain function. The compounds of the invention may accordingly be administered to a subject, e.g., a living animal body, including a human, in need of stimulation of the cognitive functions of the forebrain and hippocampus, and if desired in the form of a pharmaceutically acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically acceptable carrier or diluent, especially and preferably in the form of a pharmaceutical composition thereof, whether by oral, rectal, or parenteral (including subcutaneous) route, in an effective forebrain and hippocampus stimulating amount, and in any event an amount which is effective for improving the cognitive function of mammals due to their muscarinic cholinergic receptor agonistic activity. Suitable dosage ranges are 1–100 milligrams daily, 10–100 milligrams daily, and especially 30–70 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples:

EXAMPLE 1

3-(3-Chloro-1,2,5-thiadiazol-4-yl)pyridine

To a solution of sulfurmonochloride (2.4 ml, 30 mmol) in N,N-dimethylformamide (5 ml) was slowly added alpha-aminoalpha(3-pyridyl)acetonitrile (Archive der Pharmazie 289 (4) (1956)) (1.70 g, 10 mmol). The reaction mixture was stirred at room temperature for 18 h. Water (20 ml) was added and the aqueous phase was extracted with ether and the ether phase discharged. A 50% potassium hydroxide solution was added to the aqueous phase to pH>9. The aqueous phase was extracted several times with ether and the ether phases were dried and evaporated. The residue was purified by column chromatography (SiO$_2$, eluent: ethyl acetate/methylene chloride (1:1)). The title compound was collected in 45% (880 mg) yield. M$^+$: 197.

EXAMPLE 2

A. 3-(3-(5-Cyanopentylthio)-1,2,5-thiadiazol-4-yl)pyridine

Sodium hydrogen sulfide monohydrate (0.25 g, 3.3 mmol) was added to a solution of 3-(3-chloro-1,2,5-thiadiazol-4-yl)pyridine (0.59 g, 3.0 mmol) in DMF (20 ml) at room temperature and the reaction mixture was stirred for 1 h. Potassium carbonate (1.24 g, 9 mmol) and 6-bromocapronitrile (0.80 g, 4.5 mmol) were added and the reaction mixture was stirred for additionally 24 h. Water (50 ml) was added and extracted with ether. The combined ether phases were dried and evaporated to give the title compound.

B. 3-(3-(5-Cyanopentylthio)-1,2,5-thiadiazol-4-yl)-1-methylpyridinium iodide Methyl iodide (1 ml, 15 mmol) was added to a solution of 3-(3-(5-cyanopentylthio)-1,2,5-thiadiazol-4-yl)pyridine (3 mmol) in acetone and the reaction mixture was stirred at room temperature for 20 h. and evaporated.

C. 3-(3-(5-Cyanopentylthio)-1,2,5-thiadiazol-4-yl)-1,2,5,6-tetrahydro-1-methylpyridine oxalate Sodium borohydride (290 mg, 7.5 mmol) was added to a solution of 3-(3-(5-cyanopentylthio)-1,2,5-thiadiazol-4-yl)-1-methylpyridinium iodide (3 mmol) in ethanol (99.9%, 20 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 410 mg. M.p. 139–140° C. Compound 1.

The following compounds were made in exactly the same manner, starting with the appropriate alkyl halogenide:

3-(3-(3-Chloropropylthio)-1,2,5-thiadiazol-4-yl)-1,2,5,6-tetrahydro-1-methylpyridine oxalate. M.p. 136–138° C. Compound 2.

3-(3-(3-Cyanopropylthio)-1,2,5-thiadiazol-4-yl)-1,2,5,6-tetrahydro-1-methylpyridine oxalate. M.p. 117.5–118° C. Compound 3.

3-(3-(3-Phenylpropylthio)-1,2,5-thiadiazol-4-yl)-1,2,5,6-tetrahydro-1-methylpyridine oxalate. M.p. 110–110.5° C. Compound 4.

3-(3-(2-Phenoxyethylthio)-1,2,5-thiadiazol-4-yl)-1,2,5,6-tetrahydro-1-methylpyridine oxalate. M.p. 125.5–126° C. Compound 5.

3-(3-(4-Cyanobutylthio)-1,2,5-thiadiazol-4-yl)-1,2,5,6-tetrahydro-1-methylpyridine oxalate. M.p. 127–127.5° C. Compound 6.

3-(3-(8-Hydroxyoctylthio)-1,2,5-thiadiazol-4-yl)-1,2,5,6-tetrahydro-1-methylpyridine oxalate. M.p. 112.5–113.5° C. Compound 7.

3-(3-(4-Chlorobutylthio)-1,2,5-thiadiazol-4-yl)-1,2,5,6-tetrahydro-1-methylpyridine oxalate. M.p. 136–137° C. Compound 8.

3-(3-(4,4-Bis-(4-fluorophenyl)-butylthio)-1,2,5-thiadiazol-4-yl)-1,2,5,6-tetrahydro-1-methylpyridine oxalate. M.p. 117.5–118° C. Compound 9.

3-(3-(2-(1,3-Dioxolane-2-yl)-ethylthio)-1,2,5-thiadiazol-4-yl)-1,2,5,6-tetrahydro-1-methylpyridine oxalate. M.p. 117–118° C. Compound 10.

3-(3-(4-Cyanobenzylthio)-1,2,5-thiadiazol-4-yl)-1,2,5,6-tetrahydro-1-methylpyridine oxalate. M.p. 138–140° C. Compound 11.

3-(3-(2-Phenylethylthio)-1,2,5-thiadiazol-4-yl)-1,2,5,6-tetrahydro-1-methylpyridine oxalate. M.p. 155–156° C. Compound 12.

3-(3-(4-Bromobenzylthio)-1,2,5-thiadiazol-4-yl)-1,2,5,6-tetrahydro-1-methylpyridine oxalate. M.p. 139–140° C. Compound 13.

3-(3-(4-Methylbenzylthio)-1,2,5-thiadiazol-4-yl)-1,2,5,6-tetrahydro-1-methylpyridine oxalate. M.p. 162–165° C. Compound 14.

3-(3-(4-Pyridylmethylthio)-1,2,5-thiadiazol-4-yl)-1,2,5,6-tetrahydro-1-methylpyridine oxalate. M.p. 140–142° C. Compound 15.

3-(3-(2-Benzoylethylthio)-1,2,5-thiadiazol-4-yl)-1,2,5,6-tetrahydro-1-methylpyridine oxalate. M.p. 99–100° C. Compound 16.

3-(3-(4-Oxo-4-(4-fluorophenyl)-butylthio)-1,2,5-thiadiazol-4-yl)-1,2,5,6-tetrahydro-1-methylpyridine oxalate. M.p. 131–132° C. Compound 17.

3-(3-Benzyloxycarbonylmethylthio-1,2,5-thiadiazol-4-yl)-1,2,5,6-tetrahydro-1-methylpyridine oxalate. M.p. 179–180° C. Compound 18.

3-(3-Benzylthio-1,2,5-thiadiazol-4-yl)-1,2,5,6-tetrahydro-1-methylpyridine oxalate. M.p. 195–197° C. Compound 19.

3-(3-(4,4,4-Trifluorobutylthio)-1,2,5-thiadiazol-4-yl)-1,2,5,6-tetrahydro-1-methylpyridine oxalate. M.p. 163–165° C. Compound 20.

3-(3-(5,5,5-Trifluoropentylthio)-1,2,5-thiadiazol-4-yl)-1,2,5,6-tetrahydro-1-methylpyridine oxalate. M.p. 134–136° C. Compound 21.

3-(3-(6,6,6-Tifluorohexylthio)-1,2,5-thiadiazol-4-yl)-1,2,5,6-tetrahydro-1-methylpyridine oxalate. M.p. 128–129° C. Compound 22.

3-(3-Ethoxycarbonylpentylthio-1,2,5-thiadiazol-4-yl)-1,2,5,6-tetrahydro-1-methylpyridine oxalate. M.p. 78–81° C. Compound 23.

EXAMPLE 3

A. 3-(3-(6,6,6-Trifluorohexyloxy-1,2,5-thiadiazol-4-yl)pyridine

To a mixture of sodium hydride (12.8 mmol) and 6,6,6-trifluoro-1-hexanol (3.0 g, 19.2 mmol) in tetrahydrofuran (40 ml) was added 3-(3-chloro-1,2,5-thiadiazol-4-yl)pyridine (1.3 g, 6.4 mmol). The mixture was refluxed for 36 h. and evaporated. After evaporation the residue was dissolved in water then extracted with diethyl ether. The dried organic phases were evaporated and the residue purified by column chromatography (silica gel, eluent:ethyl acetate/hexanes) to yield 630 mg (31%) of the title compound.

B. 3-(3-(6,6,6-Trifluorohexyloxy-1,2,5-thiadiazol-4-yl)-1-methylpyridinium iodide A solution of methyl iodide (852 mg, 6.0 mmol) and 3-(3-(6,6,6-trifluorohexyloxy-1,2,5-thiadiazol-4-yl)pyridine (630 mg, 2.0 mmol) in acetone (25 ml) was refluxed for 7 h. The solution was evaporated and the residue was used directly in the next step.

C. 1,2,5,6-Tetrahydro-1-methyl-3-(3-(6,6,6-trifluorohexyloxy)-1,2,5-thiadiazol-4-yl)pyridine oxalate Sodium borohydride (380 mg, 10 mmol) was added to a solution of 3-(3-(6,6,6-trifluorohexyloxy-1,2,5-thiadiazol-4-yl)-1-methylpyridinium iodide (2.0 mmol) in ethanol (15 ml) and the reaction mixture was stirred at room temperature overnight. After evaporation the residue was dissolved in water and extracted with diethyl ether. The dried organic phases were evaporated and the residue was purified by column chromatography (silica gel, eluent: 25% ethyl acetate in hexanes). The title compound was crystallized as the oxalate salt from acetone to yield 180 mg (21%), m.p. 138–140° C. Theoretical % C=45.17, % H=5.21, % N=9.88. Found % C=45.13, % H=5.18, % N=9.62. Compound 24.

The following compounds were made in exactly the same manner using the appropriate alkoxy derivative:

1,2,5,6-Tetrahydro-1-methyl-3-(3-(3-(2-thienyl)-1-propoxy)-1,2,5-thiadiazol-4-yl)pyridine oxalate, m.p. 130–133° C., $M^+$: 321. Compound 25.

1,2,5,6-Tetrahydro-1-methyl-3-(3-(3-(4-methoxyphenyl)-1-propoxy)-1,2,5-thiadiazol-4-yl)pyridine oxalate, m.p. 166–167° C., $M^+$: 345. Compound 26.

1,2,5,6-Tetrahydro-1-methyl-3-(3-(2-(4-methoxyphenyl)-1-ethoxy)-1,2,5-thiadiazol-4-yl)pyridine oxalate, m.p. 166–167° C., $M^+$: 331. Compound 27.

1,2,5,6-Tetrahydro-1-methyl-3-(3-(2-(2-thienyl)-1-ethoxy)-1,2,5-thiadiazol-4-yl)pyridine oxalate, m.p. 145–146° C., $M^+$: 306. Compound 28.

1,2,5,6-Tetrahydro-1-methyl-3-(3-(2-(3-thienyl)-1-ethoxy)-1,2,5-thiadiazol-4-yl)pyridine oxalate, m.p. 138–140° C., $M^+$: 306. Compound 29.

1,2,5,6-Tetrahydro-1-methyl-3-(3-(3-hydroxy-1-propoxy)-1,2,5-thiadiazol-4-yl)pyridine oxalate, m.p. 105–107° C., $M^+$: 256. Compound 30.

1,2,5,6-Tetrahydro-1-methyl-3-(3-(2-phenyl-1-ethoxy)-1,2,5-thiadiazol-4-yl)pyridine oxalate, m.p. 146–147° C., $M^+$: 301. Compound 31.

1,2,5,6-Tetrahydro-1-methyl-3-(3-(2-thienylmethoxy)-1,2,5-thiadiazol-4-yl)pyridine oxalate, m.p. 161–162° C., $M^+$: 294. Compound 32.

1,2,5,6-Tetrahydro-1-methyl-3-(3-(3-hydroxy-1-hexyloxy)-1,2,5-thiadiazol-4-yl)pyridine oxalate, m.p. 147–148° C., $M^+$: 297. Compound 33.

1,2,5,6-Tetrahydro-1-methyl-3-(3-(3-thienylmethoxy)-1,2,5-thiadiazol-4-yl)pyridine oxalate, m.p. 175–176° C., $M^+$: 293. Compound 34.

1,2,5,6-Tetrahydro-1-methyl-3-(3-(3-phenyl-1-propoxy)-1,2,5-thiadiazol-4-yl)pyridine oxalate, m.p. 136–138° C., $M^+$: 315. Compound 35.

1,2,5,6-Tetrahydro-1-methyl-3-(3-(3-(2-pyrrolidon-1-yl)-1-propoxy)-1,2,5-thiadiazol-4-yl)pyridine oxalate, m.p. 160–161° C., $M^+$: 322. Compound 36.

1,2,5,6-Tetrahydro-1-methyl-3-(3-(6-acetamido-1-hexyloxy)-1,2,5-thiadiazol-4-yl)pyridine oxalate, m.p. 114–116° C., $M^+$: 338. Compound 37.

1,2,5,6-Tetrahydro-1-methyl-3-(3-(2-acetamido-1-ethoxy)-1,2,5-thiadiazol-4-yl)pyridine oxalate, m.p. 145–148° C., $M^+$: 283. Compound 38.

1,2,5,6-Tetrahydro-1-methyl-3-(3-(2-(2-pyrrolidon-1-yl)-1-ethoxy)-1,2,5-thiadiazol-4-yl)pyridine oxalate, m.p. 170–171° C., $M^+$: 309. Compound 39.

1,2,5,6-Tetrahydro-1-methyl-3-(3-(2-propionamido-1-ethoxy)-1,2,5-thiadiazol-4-yl)pyridine oxalate, m.p. 148–143° C,, $M^+$: 296. Compound 40.

1,2,5,6-Tetrahydro-1-methyl-3-(3-(2-(2-oxazolidon-3-yl)-1-ethoxy)-1,2,5-thiadiazol-4-yl)pyridine oxalate, m.p. 157–159° C., $M^+$: 310. Compound 41.

1,2,5,6-Tetrahydro-1-methyl-3-(3-(2-benzylthio-1-ethoxy)-1,2,5-thiadiazol-4-yl)pyridine oxalate, m.p. 133–134° C., $M^+$: 347. Compound 42.

1,2,5,6-Tetrahydro-1-methyl-3-(3-(3-(1-pyrrolidyl)-1-propoxy)-1,2,5-thiadiazol-4-yl)pyridineoxalate, m.p. 141–142° C., $M^+$: 308. Compound 43.

1,2,5,6-Tetrahydro-1-methyl-3-(3-(2-ureido-1-ethoxy)-1,2,5-thiadiazol-4-yl)pyridine oxalate, m.p. 200° C. (decompose), $M^+$: 265. Compound 44.

1,2,5,6-Tetrahydro-1-methyl-3-(3-(2-ethylsulfinyl-1-ethoxy)-1,2,5-thiadiazol-4-yl)pyridine oxalate 1,2,5,6-tetrahydro-1-methyl-3-(3-(2-ethylsulfinyl-1-ethoxy)-1,2,5-thiadiazol-4-yl)pyridine oxalate was prepared in the same manner using 2-(ethylthio)ethanol as the starting alcohol. The intermediate 3-(4-(2-ethylthio-1-ethoxy)-1,2,5-thiadiazol-3-yl)pyridine was oxidized with 1.1 equivalent of $NaIO_4$ and 1 equivalent $MeSO_3H$ using water as the reaction solvent. After a reaction time of 3.5 h. the solution was made basic with 2N NaOH and extracted with ethyl acetate. The combined extracts were dried over $MgSO_4$ and evaporated under vacuum. The resulting sulfoxide was then converted to the title compound in the same manner described above. M.p. 171–172° C., $M^+$: 302. Compound 45.

1,2,5,6-Tetrahydro-3-(3-(5-oxohexyl)-1,2,5-thiadiazol-4-yl)-1-methylpyridine 1,2,5,6-tetrahydro-3-(3-(5-hydroxyhexyl)-1,2,5-thiadiazol-4-yl)-1-methylpyridine was prepared in the same manner using 1,5-hexandiol. Oxidation of this compound to the named ketone was carried out under conditions as follows. To a –70° C. solution of oxalylchloride (420 μl, 4.8 mmol) in 25 ml $CH_2Cl_2$ was added DMSO (750 μl, 10.6 mmol) at a rate so as to maintain the reaction temperature below –45° C. Two min. after the addition 1,2,5,6-tetrahydro-3-(3-(5-hydroxyhexyl)-1,2,5-thiadiazol-4-yl)-1-methylpyridine (1.3 g, 4.4 mmol) in 20 ml $CH_2Cl_2$ was added slowly, keeping the temperature below –45° C. After 15 min. $Et_3N$ (3 ml, 21.8 mmol) was added and the reaction was warmed to room temperature. Brine (50 ml) was added and the mixture was extracted three times with 50 ml $CH_2Cl_2$. The combined extracts were dried over $Na_2SO_4$ and evaporated under vacuum. The resulting oil was chromatographed on silica gel (90% $CHCl_3$, 2% MeOH as eluent), affording 810 mg of an oil, which was dissolved in MeOH and treated with oxalic acid (250 mg, 2.8 mmol). The resulting oxalate salt was recrystallized from MeOH/EtOAc, affording 860 mg. M.p. 143–144° C., $M^+$: 295. Compound 46.

EXAMPLE 4

A. Alpha-oximido-3-pyridylacetonitrile 3-pyridylacetonitrile (47.2 g, 400 mmol) was dissolved in a solution of sodium hydroxide (16 g, 400 mmol) in methanol (100 ml). Methylnitrite, generated by dropping a solution of concentrated sulphuric acid (12.8 ml) and water (26 ml) to a solution of sodium nitrite (33.2 g, 480 mmol) in water (20 ml) and methanol (20 ml), was bobbled through the 3-pyridylacetonitrile solution at 0° C. The reaction mixture was stirred at 0° C. for 1 h. and the precipitate collected by filtration. The precipitate was washed with a little methanol to give the wanted product in 70% (41.1 g) yield. M+: 147.

B. Alpha-oximido-3-pyridylacetamidoxime

A mixture of alpha-oximido-3-pyridylacetonitrile (41.0 g, 279 mmol), hydroxylamine hydrochloride (21.5 g, 310 mmol) and sodium acetate (50.8 g, 620 mmol) in ethanol (99.9%, 500 ml) was refluxed for 4 h. After cooling, the precipitate was collected by filtration and dried. The precipitate contained the wanted product and sodium acetate (85 g, 168%); M+: 180.

C. 3-(3-amino-1,2,5-oxadiazol-4-yl)pyridine

Crude alpha-oximido-3-pyridylacetamidoxime (5 g) and phosphorus pentachloride (5 g) was refluxed in dry ether (250 ml) for 6 h. Water and potassium carbonate to alkaline pH was added and the phases separated. The aqueous phase was extracted with ether and the combined ether phases dried. Evaporation of the ether phases gave the title compound in 850 mg yield; M+: 162.

D. 3-(3-chloro-1,2,5-oxadiazol-4-yl)pyridine

To a solution of 3-(3-amino-1,2,5-oxadiazol-4-yl)pyridine (1.0 g, 6.2 mmol) in glacial acetic acid (16 ml) and concentrated hydrochloric acid (5.2 ml) was added $CuCl_2$ (938 mg, 7 mmol) and copper coils (100 mg) at 0° C. After 10 min. a solution of sodium nitrite (483 mg, 7 mmol) in water (3 ml) was added dropwise at 5° C. The reaction mixture was stirred additionally 30 min. at 0° C. Aqueous sodium hydroxide (2 N) was added to alkaline pH and the mixture extracted with ether. The ether phases were dried and evaporated to give a mixture of the title compounds. Separation by column chromatography ($SiO_2$, eluent:ethyl acetate) gave the chloro compound, upper spot, in 230 mg yield.

E. 3-(3-(3-phenylpropylthio)-1,2,5-oxadiazol-4-yl) pyridine

Sodium hydrogen sulfide monohydrate (0.74 g, 10.5 mmol) was added to a solution of 3-(3-chloro-1,2,5-oxadiazol-4-yl)pyridine (1.27, 7.0 mmol) in DMF (30 ml) at room temperature and the reaction mixture was stirred for 1 h. Potassium carbonate (2.0 g, 14.5 mmol) and 1-bromo-3-phenylpropane (2.4 g, 12 mmol) were added and the reaction mixture was stirred for additionally 24 h. Water (50 ml) was added and extracted with ether. The combined ether phases were dried and evaporated.

Purification by column chromatography ($Sio_2$, eluent::ethyl acetate/methylene chloride (1:1)) gave the title compound.

F. 3-(3-(3-phenylpropylthio)-1,2,5-oxadiazol-4-yl)-methylpyridinium iodide

Methyl iodide (1 ml, 15 mmol) was added to a solution of 3-(3-(3-phenylpropylthio)-1,2,5-oxadiazol-4-yl)pyridine (7 mmol) in acetone and the reaction mixture was stirred at room temperature for 20 h. and evaporated.

G. 3-(3-(3-phenylpropylthio)-1,2,5-oxadiazol-4-yl)-1,2,5,6-tetrahydro-1-methylpyridine oxalate Sodium borohydride (650 mg, 17 mmol) was added to a solution of 3-(3-(3-phenylpropylthio)-1,2,5-oxadiazol-4-yl)-1-methylpyridinum iodide (7 mmol), in ethanol (99.9%, 20 ml) and the reaction mixture was stirred at −10° C. for 1 h. After evaporation the residue was dissolved in water and extracted with ethyl acetate. The dried organic phases were evaporated and the residue purified by column chromatography ($SiO_2$, eluent:ethyl acetate/methanol (4:1)). The title compound was crystallized as the oxalate salt from acetone and recrystallized to yield 170 mg. M.p. 106–108° C. Compound 47.

The following compound was made in exactly the same manner using the appropriate alkylhalogenide:

3-(3-(2-phenoxyethylthio)-1,2,5-oxadiazol-4-yl)-1,2,5,6-tetrahydro-1-methylpyridine oxalate, m.p. 122–124° C. Compound 48.

EXAMPLE 5

1-(3-(3-Pyridyl)-1,2,5-thiadiazol-4-ylthio)-4-(3-(1-methyl-1,2,5,6-tetrahydropyridin-3-yl)-1,2,5-thiadiazol-4-ylthio) butane oxalate To a solution of 3-(3-chloro-1,2,5-thiadiazol-4-yl)-1-methyl-1,2,5,6-tetrahydropyridine (EP 0384288) (0.43 g, 2 mmol) in DMF (30 ml) was added sodiumhydrogensulfide (0.3 g, 4 mmol). The reaction mixture was stirred at room temperature for 1 h. Potassium carbonate (1 g) and 3-(3-(4-chlorobutylthio)-1,2,5-thiadiazol-4-yl)-pyridine were added and the reaction mixture stirred at room temperature overnight. Water (200 ml) was added and the water phase extracted with ether (3×100 ml). The ether extracts were dried over magnesium sulfate and evaporated. The residue was purified by column chromatography (eluent:ethyl acetate/methanol 9:1). The free base obtained was crystallized with oxalic acid from acetone in 0.9 g yield. (Compound 49). M.p. 127–129° C.

EXAMPLE 6

1-(1-Methyltetrazol-5-ylthio)-4-(3-(1-methyl-1,2,5, 6-tetrahydropyridin-3-yl)-1,2,5-thiadiazol-4-ylthio) butaneoxalate To a solution of 3-(3-(4-chlorobutylthio)-1,2,5-thiadiazol-4-yl)-1-methyl-1,2,5,6-tetrahydropyridine (0.30 g, 1 mmol) in DMF (30 ml) were added 1-methyl-5-mercaptotetrazol (0.35 g, 3 mmol) and potassium carbonate (2 g). The reaction mixture was stirred at room temperature for 60 h. 1 N hydrochloric acid was added (200 ml) and the water phase was extracted with ether (2×100 ml). The water phase was basified with solid potassium carbonate and extracted with ether (3×100 ml). The ether extracts from the alkaline extractions were combined and dried over magnesium sulfate. The ether phase was evaporated and the residue was crystallized with oxalic acid from acetone giving the title compound in 0.4 g yield. (Compound 50). M.p. 77–79° C.

EXAMPLE 7

The following compounds were made in exactly the same manner as described in example 6 by using the reagents indicated.

1-(2-Methyl-1,3,4-thiadiazol-5-ylthio)-4-(3-(1-methyl-1, 2,5,6-tetrahydropyridin-3-yl)-1,2,5-thiadiazol-4-ylthio) butane oxalate from 3-(3-(4-chlorobutylthio)-1,2,5-thiadiazol-4-yl)-1-methyl-1,2,5,6-tetrahydropyridine and 2-methyl-5-mercapto-1,3,4-thiadiazole. (Compound 51). M.p. 102–104° C. 1-(2-Thiazolin-2-ylthio)-4-(3-(1-methyl-1,2,5,6-tetrahydropyridin-3-yl)-1,2,5-thiadiazol-4-ylthio) butaneoxalate from 3-(3-(4-chlorobutylthio)-1,2,5- thiadiazol-4-yl)-1-methyl-1,2,5,6-tetrahydropyridine and 2-thiazoline-2-thiol. (Compound 52). M.p. 116–117° C.

1-(2-Benzoxazolylthio)-4-(3-(1-methyl-1,2,5,6-tetrahydropyridin-3-yl)-1,2,5-thiadiazol-4-ylthio) butaneoxalate from 3-(3-(4-chlorobutylthio)-1,2,5-thiadiazol-4-yl)-1-methyl-1,2,5,6-tetrahydropyridine and 2-mercaptobenzoxazole. (Compound 53). M.p. 156–158° C.

1-(2-Methyl-1,3,4-thiadiazol-5-ylthio)-5-(3-(1-methyl-1,2,5,6-tetrahydropyridin-3-yl)-1,2,5-thiadiazol-4-ylthio) pentane oxalate from 3-(3-(5-chloropentylthio)-1,2,5-thiadiazol-4-yl)-1-methyl-1,2,5,6-tetrahydropyridine and 2-methyl-5-mercapto-1,3,4-thiadiazole. (Compound 54). M.p. 69–70° C.

1-(2-Benzthiazolylthio)-5-(3-(1-methyl-1,2,5,6-tetrahydropyridin-3-yl)-1,2,5-thiadiazol-4-ylthio)pentane oxalate from 3-(3-(5-chloropentylthio)-1,2,5-thiadiazol-4-yl)-1-methyl-1,2,5,6-tetrahydropyridine and 2-mercaptobenzthiazole. (Compound 55). M.p. 116–117° C.

1-(1-Methyltetrazol-5-ylthio)-5-(3-(1-methyl-1,2,5,6-tetrahydropyridin-3-yl)-1,2,5-thiadiazol-4-ylthio)pentane oxalate from 3-(3-(5-chloropentylthio)-1,2,5-thiadiazol-4-yl)-1-methyl-1,2,5,6-tetrahydropyridine and 1-methyl-5-mercaptotetrazole. (Compound 56). M.p. 96–97° C.

1-(2-Methyl-1,3,4-thiadiazol-5-ylthio)-6-(3-(1-methyl-1,2,5,6-tetrahydropyridin-3-yl)-1,2,5-thiadiazol-4-ylthio) hexane oxalate from 3-(3-(6-chlorohexylthio)-1,2,5-thiadiazol-4-ylthio)hexane oxalate from 3-(3-(6-chlorohexylthio)-1,2,5-thiadiazol-4-yl)-1-methyl-1,2,5,6-tetrahydropyridine and 2-methyl-5-mercapto-1,3,4-thiadiazole. (Compound 57). M.p. 85–86° C.

1-(1-Methyltetrazol-5-ylthio)-6-(3-(1-methyl-1,2,5,6-tetrahydropyridin-3-yl)-1,2,5-thiadiazol-4-ylthio) hexaneoxalate from 3-(3-(6-chlorohexylthio)-1,2,5-thiadiazol-4-yl)-1-methyl-1,2,5,6-tetrahydropyridine and 1-methyl-5-mercaptotetrazole. (Compound 58). M.p. 65–66° C.

1-(2-Thiazolin-2-ylthio)-6-(3-(1-methyl-1,2,5,6-tetrahydropyridin-3-yl)-1,2,5-thiadiazol-4-ylthio) hexaneoxalate from 3-(3-(6-chlorohexylthio)-1,2,5-thiadiazol-4-yl)-1-methyl-1,2,5,6-tetrahydropyridine and 2-thiazoline-2-thiol. (Compound 59). M.p. 61–62° C.

EXAMPLE 8

3-(3-Methylsulfonyl-1,2,5-thiadiazol-4-yl)-1,2,5,6-tetrahydro-1-methylpyridine oxalate hemiacetone A solution of 3-(3-methylthio-1,2,5-thiadiazol-4-yl)-1,2,5,6-tetrahydro-1-methylpyridine oxalate (0.25 g, 0.0079 mol) in $H_2O$ (10 ml) was cooled in an ice-water bath as a solution of oxone (0.7 g, 0.00114 mol) in $H_2O$ (5 ml) was added dropwise. Cooling was removed and after 5 h excess $NaHSO_3$ was added. The solution was cooled in an ice-water bath, the solution made basic, and the mixture extracted with $CH_2Cl_2$ (3×25 ml). The extracts were dried, the solvent evaporated, and the residue purified by radial chromatography (5% EtOH-0.5% $NH_4OH$—$CHCl_3$) to give a white crystalline solid (0.2 g). The oxalate salt recrystallized from acetone to give colorless crystals. M.p. 96–97.5° C. (Compound 60). Analysis and NMR confirmed that the salt contained 0.5 mol of acetone. Analysis $C_9H_{13},N_3O_2S$—$C_2H_2O_4$-0.5 $C_3H_6O$, C,H,N; Theory C, 39.68; H, 4.79; N, 11.10; Found C, 39.52; H, 4.85; N, 11.19.

3-(3-[2-(1-Pyrrolidinyl)ethoxy]-1,2,5-thiadiazol-4-yl)-1,2,5,6-tetrahydro-1-methylpyridine dioxalate A suspension of NaH (0.0075 mol) in THF (25 ml) was treated with 2-hydroxyethylpyrrolidine (1 ml, 0.0086 mol) and after 30 min. the free base of (Compound 60) (0.6 g, 0.0023 mol), was added. After another hour, $H_2O$ (2 ml) was added and the solvent evaporated. The residue was suspended in $H_2O$ and extracted with $CH_2Cl_2$ (3×25 ml). The extracts were dried, the solvent evaporated, and the residue purified by radial chromatography (20% EtOH-2% $NH_4OH$—$CHCl_3$) to give a straw colored liquid (0.4 g). The dioxalate salt recrystallized from EtOH to give a white solid. M.p. 186–188° C. (Compound 61). Analysis $C_{14}H_{22},N_4OS$-$2C_2H_2O_4$, C,H,N; Theory C, 45.57; H, 5.52; N, 11.81; Found C, 45.53; H, 5.50; N, 11.61.

EXAMPLE 9

3-(3-(3-(5-Methyl-2-thienyl)-1-propoxy)-1,2,5-thiadiazol-4-yl)-1,2,5,6-tetrahydro-1-methylpyridine oxalate Sodium hydride (10.2 mmol) was added to a solution of 3-(5-methyl-2-thienyl)-1-propanol (4.0 g, 25.5 mmol) in THF (40 ml). The mixture was stirred for 1 h at room temperature, whereupon a solution of 3-(3-chloro-1,2,5-thiadiazol-4-yl)pyridine (EP 0384288) (1.0 g, 5.1 mmol) in THF (10 ml) was added dropwise to the reaction mixture. After stirring overnight at room temperature, the reaction was quenched with water then extracted with diethyl ether. The organic phase was dried over $NaCl/Na_2So_4$ then evaporated to yield crude 3-(3-(5-methyl-2-thienyl)propoxy-1,2,5-thiadiazol-4-yl)pyridine. A solution of 3-(3-(5-methyl-2-thienyl)propoxy-1,2,5-thiadiazol-4-yl)pyridine (1.0 g, 3.2 mmol) and iodomethane (2.3 g, 16.0 mmol) in 60 ml of acetone was refluxed overnight. The solution was evaporated to yield 1.5 g of the quaternized product. Sodium borohydride (0.6 g, 16.0 mmol) was carefully added to a solution of the quaternized product (1.5 g) in ethanol (30 ml). The reaction was evaporated and the resulting residue was taken up in water and extracted with methylene chloride (3×100 ml). The organic phase was dried over $NaCl/Na_2SO_4$ then evaporated. The residue was purified by radial chromatography eluting with 0.5% $NH_4OH/5.0%$ EtOH in $CHCl_3$. The oxalate salt was made to yield 337 mg of the title compound. M.p. 134–137° C. (Compound 62).

The following compounds were made in the same manner as described above using the indicated alcohol instead of 3-(5-methyl-2-thienyl)-1-propanol:

3-(3-( (5-Propyl-2-thienyl)methoxy)-1,2,5-thiadiazol-4-yl)-1,2,5,6-tetrahydro-1-methylpyridine oxalate (Compound 63) from (5-propyl-2-thienyl)-methanol. M.p. 134–135° C.

3-(3-(3-(5-Pentyl-2-thienyl)-1-propoxy)-1,2,5-thiadiazol-4-yl)-1,2,5,6-tetrahydro-1-methylpyridine oxalate (Compound 64) from 3-(5-pentyl-2-thienyl)-1-propanol. M.p. 138–140° C.

3-(3-(3-(2-Thienylthio)-1-propoxy)-1,2,5-thiadiazol-4-yl)-1,2,5,6-tetrahydro-1-methylpyridine oxalate (Compound 65) from 3-(2-thienylthio)-1-propanol. M.p. 102–110° C.

EXAMPLE 10

3-(3-(3-(2-Thienyl)-1-propylthio)-1,2,5-thiadiazol-4-yl)-1,2,5,6-tetrahydro-1-methylpyridine oxalate A solution of 3-(3-chloro-1,2,5-thiadiazol-4-yl)pyridine (2.0 g, 10.1 mmol) in DMF (10 ml) was cooled to 5° C. whereupon potassium carbonate (2.8 g, 20.2 mmol) and sodium hydrosulfide monohydrate (1.5 g, 20.2 mmol) were added to the reaction. Stirred for 1 h then potassium carbonate (1.4 g, 10.1 mmol) and a solution of 3-(2-thienyl)-1-chloro-propane (1.8 g, 11.2 mmol) in DMF (5 ml) were added to the reaction and stirred for 1 h at room temperature. The reaction was quenched with water then extracted with methylene chloride (3×75 ml). The organic phase was dried over NaCl/Na₂SO₄ then evaporated. The residue was purified by flash chromatography eluting with 1:1 ethyl acetate/hexanes to yield 1.0 g of 3-(3-(3-(2-thienyl)-1-propylthio)-1,2,5-thiadiazol-4-yl)pyridine. Quaternization and reduction was done as described in example 9. (Compound 66). M.p. 98–100° C.

The following compounds were made in exactly the same manner as described above using the indicated alkylhalogenide:

3-(3-(2-Thienylmethylthio)-1,2,5-thiadiazol-4-yl)-1,2,5,6-tetrahydro-l-methylpyridine oxalate (Compound 67) using (2-thienyl)-chloromethane. M.p. 131–135° C.

3-(3-(3-(2-Oxazolidinon-3-yl)-1-propylthio)-1,2,5-thiadiazol-4-yl)-1,2,5,6-tetrahydro-l-methylpyridine oxalate (Compound 68) using 3-(2-oxazolidinon-3-yl)-1-chloropropane. M.p. 104–109° C.

3-(3-(3-(2-Thiazolidinon-3-yl)-1-propylthio-1,2,5-thiadiazol-4-yl)-1,2,5,6-tetrahydro-1-methylpyridine oxalate (Compound 69) using 3-(2-thiazolidinon-3-yl)-1-chloropropane. M.p. 75–81° C.

3-(3-(5-Pentyl-2-thienyl)methylthio-1,2,5-thiadiazol-4-yl)-1,2,5,6-tetrahydro-1-methylpyridine oxalate (Compound 70) using (5-pentyl-2-thienyl)chloromethane. M.p. 143–146° C.

(R)-(+) 3-(3-(3-(4-Benzyl-2-oxazolidinon-3-yl)-1-propylthio)-1,2,5-thiadiazol-4-yl)-1,2,5,6-tetrahydro-1-methylpyridine oxalate (Compound 71) using (R) 3-(4-benzyl-2-oxazolidinon-3-yl)-1-chloropropane. M.p. 124–133° C.

(S)-(−) 3-(3-(3-(4-Benzyl-2-oxazolidinon-3-yl)-1-propylthio)-1,2,5-thiadiazol-4-yl)-1,2,5,6-tetrahydro-1-methylpyridine oxalate (Compound 72) using (S)-3-(4-benzyl-2-oxazolidinon-3-yl)-1-chloropropane. M.p. 132–135° C.

(4R,5S)-3-(3-(3-(4-Methyl-5-phenyl-2-oxazolidinon-3-yl)-1-propylthio)-1,2,5-thiadiazol-4-yl)-1,2,5,6-tetrahydro-1-methylpyridine oxalate (Compound 73) using (4R, 5S)-3-(4-methyl-5-phenyl-2-oxazolidinon-3-yl)-1-chloropropane. M.p. 102–106° C.

(S)-3-(3-(3-(4-Isopropyl-2-oxazolidinon-3-yl)-1-propylthio)-1,2,5-thiadiazol-4-yl)-1,2,5,6-tetrahydro-1-methylpyridine oxalate (Compound 74) using (S)-3-(4-isopropyl-2-oxazolidinon-3-yl)-1-chloropropane. M.p. 75–79° C.

(S)-3-(3-(3-(4-Ethyl-2-oxazolidinon-3-yl)-1-propylthio)-1,2,5-thiadiazol-4-yl)-1,2,5,6-tetrahydro-1-methylpyridine oxalate (Compound 75) using (S)-3-(4-ethyl-2-oxazolidinon-3-yl)-1-chloropropane. M.p. 69–71° C.

(S)-3-(3-(3-(4-(2-Butyl)-2-oxazolidinon-3-yl)-1-propylthio-1,2,5-thiadiazol-4-yl)-1,2,5,6-tetrahydro-1-methylpyridine oxalate (Compound 76) using (S)-3-(4-(2-butyl)-2-oxazolidinon-3-yl)-1-chloropropane. M.p. 77–80° C.

3-(3-(3-(4-Propyl-2-oxazolidinon-3-yl)-1-propylthio)-1,2,5-thiadiazol-4-yl)-1,2,5,6-tetrahydro-1-methylpyridine oxalate (Compound 77) using 3-(4-propyl-2-oxazolidinon-3-yl)-1-chloropropane. M.p. 65–68° C.

What is claimed is:

1. A compound of formula I (I)

wherein
  $Z^1$ is oxygen or sulphur;
  R is $-Z^2R^2SOR^2$, $SOR^2$, $SO_2R^2$, or $-Z^2R^2NHCONH_2$, wherein $Z^2$ is oxygen or sulphur, and $R^2$ is straight or branched $C_{1-15}$-alkyl, straight or branched $C_{2-5}$-alkenyl, or straight or branched $C_{2-15}$-alkynyl, each of which is optionally substituted with halogen, —OH, —CN, —CF₃, or one or two phenyl, phenoxy, benzoyl, or benzyloxycarbonyl groups wherein each aromatic group is optionally substituted with halogen, —CN, $C_{1-4}$-alkyl or $C_{1-4}$-alkoxy; and
  $R^1$ is hydrogen, straight or branched $C_{1-5}$-alkyl, straight or branched $C_{2-5}$-alkenyl or straight or branched $C_{2-5}$-alkynyl; or
a pharmaceutically acceptable salt thereof.

2. A compound according to claim 1 wherein $Z^1$ is sulphur.

3. A compound according to claim 1 which is:
  1,2,5,6-Tetrahydro-1-methyl-3-(3-(2-ureido-1-ethoxy)-1,2,5-thiadiazol-4-yl)pyridine;
  1,2,5,6-Tetrahydro-1-methyl-3-(3-(2-ethylsulfinyl-1-ethoxy)-1,2,5-thiadiazol-4-yl)pyridine; or
a pharmaceutically acceptable salt thereof.

4. A pharmaceutical composition comprising a compound according to claim 1 together with a pharmaceutically acceptable carrier or diluent.

5. The pharmaceutical composition according to claim 4 in the form of an oral dosage unit or a parenteral dosage unit.

6. The pharmaceutical composition according to claim 5, wherein the dosage unit comprises about 1 to about 100 mg of the compound.

7. A method of treating Alzheimer's disease comprising administering to a subject in need thereof an effective amount of a compound according to claim 1.

8. A method of treating glaucoma comprising administering to a subject in need thereof an effective amount of a compound according to claim 1.

9. A method of providing an analgesic effect comprising administering to a subject in need thereof an effective amount of a compound according to claim 1.

10. A method of treating Alzheimer's disease comprising administering to a subject in need thereof a pharmaceutical composition according to claim 4.

11. A method of treating glaucoma comprising administering to a subject in need thereof a pharmaceutical composition according to claim 4.

12. A method of providing an analgesic effect comprising administering to a subject in need thereof a pharmaceutical composition according to claim 4.

13. A compound which is:
  3-(3-(3-Phenylpropylthio)-1,2,5-oxadiazol-4-yl)-1,2,5,6-tetrahydro-1-methylpyridine;
  3-(3-(2-Phenoxyethylthio)-1,2,5-oxadiazol-4-yl)-1,2,5,6-tetrahydro-1-methylpyridine;

or a pharmaceutically acceptable salt thereof.

14. A compound which is:

3-(3-(4,4,4-Trifluorobutylthio)-1,2,5-thiadiazol-4-yl)-1,2,5,6-tetrahydro-1-methylpyridine;

3-(3-(5,5,5-Trifluoropentylthio)-1,2,5-thiadiazol-4-yl)-1,2,5,6-tetrahydro-1-methylpyridine;

3-(3-(6,6,6-Trifluorohexylthio)-1,2,5-thiadiazol-4-yl)-1,2,5,6-tetrahydro-1-methylpyridine;

3-(3-Ethoxycarbonylpentylthio-1,2,5-thiadiazol-4-yl)-1,2,5,6-tetrahydro-1-methylpyridine;

1,2,5,6-Tetrahydro-1-methyl-3-(3-(6,6,6-Trifluorohexyloxy)-1,2,5-thiadiazol-4-yl)pyridine;

1,2,5,6-Tetrahydro-1-methyl-3-(3-(3-hydroxy-1-propoxy)-1,2,5-thiadiazol-4-yl)pyridine;

1,2,5,6-Tetrahydro-1-methyl-3-(3-(2-phenyl-1-ethoxy)-1,2,5-thiadiazol-4-yl)pyridine;

1,2,5,6-Tetrahydro-1-methyl-3-(3-(3-hydroxy-1-hexyloxy)-1,2,5-thiadiazol-4-yl)pyridine;

1,2,5,6-Tetrahydro-1-methyl-3-(3-(3-phenyl-1-propoxy)-1,2,5-thiadiazol-4-yl)pyridine;

1,2,5,6-Tetrahydro-1-methyl-3-(3-(6-acetamido-1-hexyloxy)-1,2,5-thiadiazol-4-yl)pyridine;

1,2,5,6-Tetrahydro-1-methyl-3-(3-(2-acetamido-1-ethoxy)-1,2,5-thiadiazol-4-yl)pyridine;

1,2,5,6-Tetrahydro-1-methyl-3-(3-(2-propionamido-1-ethoxy)-1,2,5-thiadiazol-4-yl)pyridine;

1,2,5,6-Tetrahydro-1-methyl-3-(3-(2-benzylthio-1-ethoxy)-1,2,5-thiadiazol-4-yl)pyridine;

1,2,5,6-Tetrahydro-3-(3-(5-oxohexyl)-1,2,5-thiadiazol-4-yl)-1-methylpyridine; or a pharmaceutically acceptable salt thereof.

15. A compound of formula I

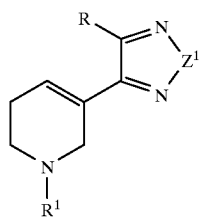

(I)

wherein $Z^1$ is oxygen or sulphur;

R is —$Z^2R^2$, wherein $Z^2$ is oxygen or sulphur, and $R^2$ is straight or branched $C_{1-15}$-alkyl, straight or branched $C_{2-15}$-alkenyl, or straight or branched $C_{2-15}$-alkynyl, each of which is substituted with one or two phenyl, phenoxy, benzoyl, or benzyloxycarbonyl groups wherein each aromatic group is substituted with $C_{1-4}$-alkoxy; and $R^1$ is hydrogen, straight or branched $C_{1-5}$-alkyl, straight or branched $C_{2-5}$-alkenyl or straight or branched $C_{2-5}$-alkynyl; or a pharmaceutically acceptable salt thereof.

16. A compound according to claim 15 which is:

1,2,5,6-Tetrahydro-1-methyl-3-(3-(3-(4-methoxyphenyl)-1-propoxy)-1,2,5-thiadiazol-4-yl)pyridine;

1,2,5,6-Tetrahydro-1-methyl-3-(3-(2-(4-methoxyphenyl)-1-ethoxy)-1,2,5-thiadiazol-4-yl)pyridine; or a pharmaceutically acceptable salt thereof.

17. A pharmaceutical composition comprising an effective amount of a compound according to claim 15 together with a pharmaceutically-acceptable carrier or diluent.

18. The pharmaceutical composition according to claim 17 in the form of an oral dosage unit or a parenteral dosage unit.

19. The pharmaceutical composition according to claim 18, wherein the dosage unit comprises about 1 to about 100 mg of the compound.

20. A method of treating Alzheimer's disease comprising administering to a subject in need thereof an effective amount of a compound according to claim 15.

21. A method of treating glaucoma comprising administering to a subject in need thereof an effective amount of a compound according to claim 15.

22. A method of providing an analgesic effect comprising administering to a subject in need thereof an effective amount of a compound according to claim 15.

23. A method of treating Alzheimer's disease comprising administering to a subject in need thereof a pharmaceutical composition according to claim 17.

24. A method of treating glaucoma comprising administering to a subject in need thereof a pharmaceutical composition according to claim 17.

25. A method of providing an analgesic effect comprising administering to a subject in need thereof a pharmaceutical composition according to claim 17.

* * * * *

UNITED STATES PATENT AND TRADEMARK OFFICE
CERTIFICATE OF CORRECTION

PATENT NO.    :    5,919,805

DATED    :    July 6, 1999

INVENTOR(S)    :    Sauerberg et al.

It is certified that error appears in the above-identified patent and that said Letters Patent is hereby corrected as shown below:

Col. 16, line 18, claim 1, delete "$C_{2-5}$" and insert -- $C_{2-15}$ --;

Signed and Sealed this

Eighteenth Day of January, 2000

Attest:

Q. TODD DICKINSON

Attesting Officer    Commissioner of Patents and Trademarks